United States Patent
Gajda et al.

[11] Patent Number: 6,162,416
[45] Date of Patent: Dec. 19, 2000

[54] ZEOLITE BETA AND ITS USE IN AROMATIC ALKYLATION

[75] Inventors: Gregory J. Gajda, Mt. Prospect, Ill.; Richard T. Gajek, Daphne, Ala.

[73] Assignee: UOP LLC, Des Plaines, Ill.

[21] Appl. No.: 09/256,987

[22] Filed: Feb. 24, 1999

Related U.S. Application Data

[63] Continuation-in-part of application No. 08/978,414, Nov. 25, 1997, abandoned, which is a continuation-in-part of application No. 08/682,862, Jul. 12, 1996, Pat. No. 5,723,710.

[51] Int. Cl.[7] .............................. C01B 33/36; C01F 7/00; B01J 29/04
[52] U.S. Cl. .................. 423/714; 423/DIG. 27; 502/85; 502/86
[58] Field of Search ................ 502/85, 86; 423/714, 423/DIG. 27

[56] References Cited

U.S. PATENT DOCUMENTS

| | | | |
|---|---|---|---|
| 4,582,815 | 4/1986 | Bowes | 502/64 |
| 4,665,255 | 5/1987 | Chang et al. | 585/467 |
| 4,891,458 | 1/1990 | Innes et al. | 585/323 |
| 5,030,786 | 7/1991 | Shamshoum et al. | 585/467 |
| 5,081,323 | 1/1992 | Innes et al. | 484/449 |
| 5,200,168 | 4/1993 | Apelian et al. | 423/714 |
| 5,310,534 | 5/1994 | Fajula et al. | 423/715 |
| 5,522,984 | 6/1996 | Gajda et al. | 208/120 |

FOREIGN PATENT DOCUMENTS 432814  11/1990  European Pat. Off. .

*Primary Examiner*—Marian C. Knode
*Assistant Examiner*—Thuan D. Dang
*Attorney, Agent, or Firm*—John G. Tolomei; Frank S. Molinaro

[57] ABSTRACT

There is disclosed a new form of zeolite beta which shows substantially greater stability and greater catalyst lifetime when used in the alkylation and transalkylation of aromatic compounds. The new, surface-modified zeolite beta is characterized by having surface aluminum 2p binding energies, as measured by X-ray photoelectron spectroscopy, of at least 74.8 electron volts. This surface-modified zeolite beta is prepared by treating an as synthesized and templated zeolite beta with an acid at a pH between about 0 and about 2 at a temperature up to about 125° C. for a time sufficient to modify the chemical environment of the surface aluminum atom without bringing about dealumination of the zeolite beta, then calcining the acid-treated templated material at 550–700° C. to remove the template.

4 Claims, No Drawings

ZEOLITE BETA AND ITS USE IN AROMATIC ALKYLATION

CROSS REFERENCE TO RELATED APPLICATION

This application is a continuation-in-part of our application, Ser. No. 08/978,414 filed on Nov. 25, 1997 now abandoned which in turn is a continuation-in-part of Ser. No. 08/682,862, filed Jul. 12, 1996, issued as U.S. Pat. No. 5,723,710 on Mar. 3, 1998, all of which are hereby incorporated by reference.

BACKGROUND OF THE INVENTION

This application relates to a new form of zeolite beta and to its use as a catalyst in the alkylation of aromatics. More particularly, this application relates to a zeolite beta which shows substantially greater stability and catalyst life when used in the alkylation and transalkylation of aromatics. It is contemplated that the catalysts of this invention may be particularly valuable in cumene production via alkylation of benzene with propylene. For ease and simplicity of exposition, the following description will make specific reference to the use of our catalyst in the alkylation of benzene with propylene to afford cumene, but it is to be recognized that this is done solely for the purpose of clarity and simplicity. We shall make frequent reference to the broader scope of this application for emphasis.

Cumene is a major article of commerce, with one of its principal uses being a source of phenol and acetone via its air oxidation and a subsequent acid-catalyzed decomposition of the intermediate hydroperoxide,

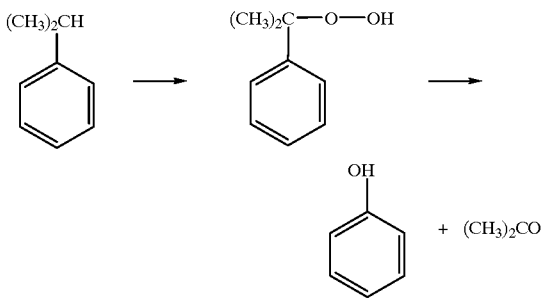

Because of the importance of both phenol and acetone as commodity chemicals, there has been much emphasis on the preparation of cumene and the literature is replete with processes for its manufacture. Certainly the most common and perhaps the most direct method of preparing cumene is the alkylation of benzene with propylene, especially using an acid catalyst. See "Encyclopedia of Chemical Processing and Design," J. J. McKetta and W. A. Cunningham, Editors, V. 14, pp 33–51 (1982). Even though a high conversion of propylene and a high selectivity to monoalkylated products are two major prerequisites of any commercially feasible process, other constraints must be satisfied.

The predominant orientation of the reaction of benzene with propylene corresponds to Markownikoff addition resulting in cumene. However, a small but very significant amount of the reaction occurs via anti-Markownikoff addition to afford n-propylbenzene (NPB). The significance of NPB formation is that it interferes with the oxidation of cumene to phenol and acetone, and consequently cumene used for oxidation must be quite pure with respect to NPB content. Since cumene and NPB are difficult to separate by conventional means, as for example distillation, a constraint in the production of cumene by the alkylation of benzene is that the n-propylbenzene formed be minimized relative to cumene. An observation pertinent to this facet of alkylation is that the relative amount of NPB formation increases with increasing temperature. Thus, from the standpoint of minimizing NPB formation it is desirable to perform the alkylation at as low a temperature as possible. Stated differently, minimizing NPB requires avoiding high reaction temperatures.

Turning to the catalysts used in aromatic alkylation, solid acid catalysts are quite desirable from the viewpoint of designing a continuous process. It is unnecessary to articulate here a litany of solid acid catalysts used in aromatic alkylation; suffice it to say that many are described and among these zeolitic catalysts have received special attention. Whatever catalyst is used, deactivation is a feature which can not be avoided but is to be minimized to the extent possible. For zeolitic catalysts deactivation usually results from the accumulation of polyalkylated products on the catalyst surface and within the zeolite channels, and it has been observed that the rate of deactivation decreases with increasing reaction temperature. Thus, minimizing catalyst deactivation generally suggests performing the alkylation at relatively high reaction temperatures. Thus it is clear that attempts to decrease catalyst deactivation by effecting reaction at high temperatures is at variance with attempts to minimize NPB formation by effecting reaction at low temperatures.

What is required in an optimum catalyst for, e.g., cumene production, is a catalyst with sufficient activity to effect alkylation at acceptable reaction rates at temperatures sufficiently low to avoid unacceptable NPB formation while exhibiting the slow catalyst deactivation usually associated with higher reaction temperatures. Because zeolite beta shows substantially greater activity than other zeolites, it has received close scrutiny as a catalyst in aromatic alkylation; see, e.g., Innes et al., U.S. Pat. No. 4,891,458, Shamshoum et al., U.S. Pat. No. 5,030,786, and EP 432,814 inter alia. However, it is found that zeolite betas as described still deactivate at unacceptably high rates at the low temperatures desired to minimize NPB formation. In order for a commercial process based on zeolite beta to become a reality it is first necessary to either increase catalyst activity—i.e., increase the rate of cumene production at a given temperature—or to decrease catalyst deactivation—i.e., increase catalyst lifetime so as to increase cumene production prior to catalyst regeneration. This application focuses on making modifications to native zeolite beta to afford a catalyst showing decreased deactivation relative to other zeolite betas.

Without wishing to be bound by any one particular theory, the rationale employed in our approach assumed catalyst deactivation resulted from polyalkylation of aromatics, perhaps with a minor contribution from oligomerization, especially where the propylene concentration is quite large. We further assumed that polyalkylates (and other deactivating materials) formed mainly as a consequence of strong acid sites on the zeolite surface. We then concluded that formation of deactivating materials could be reduced by removing the stronger acid sites on the zeolite surface, especially by converting the strong acid sites to weaker ones ineffective, or less effective, in producing deactivating materials. We have found that treating templated zeolite beta with a low concentration of a strong mineral acid followed by calcination affords a superior zeolite beta. The order of treatment is critical; acid washing a calcined zeolite beta is largely ineffective! We believe that our treatment affects only the nature of surface acid sites, as shown by an unchanged silicon:aluminum surface ratio, and a changed surface aluminum 2p binding energy as determined by x-ray photoelectron spectroscopy.

SUMMARY OF THE INVENTION

The purpose of our invention is to provide a modified zeolite beta catalyst active in the alkylation of aromatics with olefin and with deactivation rates at a given temperature less than conventional zeolite beta. An embodiment comprises a calcined, non-templated surface-modified zeolite beta, derived from an as synthesized and templated zeolite beta, having surface aluminum 2p binding energies, as measured by x-ray photoelectron spectroscopy, of at least 74.8 electron volts and having a Si/Al mole ratio within about ±2 units of the Si/Al mole ratio of the as synthesized zeolite beta. Another embodiment comprises a method of making the aforesaid surface-modified zeolite beta by treating the as synthesized and templated zeolite beta with an acid at a pH between about 0 and about 2 at a temperature from about 20° C. to about 125° C. for a time sufficient to modify the surface aluminum atoms and then calcining the acid treated templated zeolite beta at a temperature from about 550° C. to about 700° C. for a time sufficient to remove the template. Other embodiments will become apparent from the ensuing description.

DESCRIPTION OF THE INVENTION

This invention is born of the necessity to catalyze the selective monoalkylation of benzene with propylene at as low a temperature as possible while retaining the low deactivation rates manifested by zeolite beta as the catalyst at a substantially higher temperature. Once born the invention was seen to be applicable to the entire class of aromatics alkylation by olefin. The key to our invention is surface modification of zeolite beta so as to decrease the surface acidity requisite for polyalkylation, which is the major contributor to catalyst deactivation, and oligomerization, which is a minor contributor to catalyst deactivation, while retaining the acid sites necessary to catalyze the desired selective monoalkylation of aromatics. Our invention is applicable not only to the selective monoalkylation of aromatics, but also to the transalkylation of polyalkylated aromatics. Thus it is readily seen that our invention is of unusually broad scope.

In the selective monoalkylation of aromatics by olefins as catalyzed by the surface-modified zeolite beta of our invention the olefins may contain from 2 up to at least 20 carbon atoms, and may be branched or linear olefins, either terminal or internal olefins. Thus, the specific nature of the olefin is not particularly important. What the alkylations share in common is that the reactions are conducted under at least partially liquid phase conditions, a criterion readily achieved for the lower members by adjusting reaction pressures. Among the lower olefins ethylene and propylene are the most important representatives. Among the remaining olefins the class of detergent range olefins is of particular interest. This class consists of linear olefins containing from 6 up through about 20 carbon atoms which have either internal or terminal unsaturation. Linear olefins containing from 8 to 16 carbon atoms are particularly useful as detergent range olefins, and those containing from 10 up to about 14 carbon atoms are especially preferred.

Benzene is by far the most important representative of the alkylatable aromatic compounds which may be used in the practice of our invention. More generally the aromatic compounds may be selected from the group consisting of benzene, naphthalene, anthracene, phenanthrene, and substituted derivatives thereof. The most important class of substituents found on the aromatic nucleus of alkylatable aromatic compounds are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, and so forth; phenol, cresol, anisole, ethoxy-, propoxy-, butoxy-, pentoxy-, hexoxybenzene, and so forth.

In that branch of our invention where our surface-modified zeolite beta is used to catalyze selective monoalkylation of alkylatable aromatic compounds, the particular conditions under which the reaction is conducted depends upon the aromatic compound and the olefin used. Since the reaction is conducted under at least partial liquid phase conditions, reaction pressure is adjusted to maintain the olefin at least partially dissolved in the liquid phase. For higher olefins the reaction may be conducted at autogenous pressure. As a practical matter the pressure normally is in the range between about 200 and about 1,000 psig (1379–6985 kPa) but usually is in a range between about 300–600 psig (2069–4137 kPa). But we emphasize again that pressure is not a critical variable and needs to be sufficient only to maintain at least partial liquid phase conditions. Representative alkylation temperatures include a range of between 200–250° C. for alkylation of benzene with ethylene and temperatures of 90–200° C. for the alkylation of benzene by propylene. The temperature range appropriate for alkylation of the alkylatable aromatic compounds of our invention with the olefins in the C2–C20 range is between about 60 and about 400° C., with the most usual temperature range being between about 90 and 250° C.

The ratio of alkylatable aromatic compound to olefin used in the process which is our invention will depend upon the degree of selective monoalkylation desired as well as the relative costs of the aromatic and olefinic components of the reaction mixture. For alkylation of benzene by propylene, benzene-to-olefin ratios may be as low as about 1.1 and as high as about 10:1, with a ratio of 2.5:1–8:1 being preferred. Where benzene is alkylated with ethylene a benzene-to-olefin ratio between about 1:1 and 8:1 is preferred. For detergent range olefins of C6–C20, a benzene-to-olefin ratio of between 5:1 up to as high as 30:1 is generally sufficient to ensure the desired monoalkylation selectivity, with a range between about 8:1 and about 20:1 even more highly desired.

As previously alluded to, the surface modified zeolite beta of our invention also can be used to catalyze transalkylation as well as alkylation. By "transalkylation" is meant that process where an alkyl group on one aromatic nucleus is intermolecularly transferred to a second aromatic nucleus. The transalkylation of particular interest here is one where one or more alkyl groups of a polyalkylated aromatic compound is transferred to a nonalkylated aromatic compound, and is exemplified by reaction of diisopropylbenzene with benzene to afford two molecules of cumene. Thus, transalkylation often is utilized to add to the selectivity of a desired selective monoalkylation by reacting the polyalkylates invariably formed during alkylation with non-alkylated aromatic to form additional monoalkylated products. For the purposes of this section the polyalkylated aromatic compounds are those formed in the alkylation of alkylatable aromatic compounds with olefins as described above, and the nonalkylated aromatic compounds are benzene, naphthalene, anthracene, and phenanthrene. The reaction conditions for transalkylation are similar to those for alkylation, with temperatures being in the range of 100 to about 250°, pressures in the range of 100 to about 750 psig, and the molar ratio of unalkylated aromatic to polyalkylated aromatic being in the range from about 1 to about 10. Examples of polyalkylated aromatics which may be reacted with, e.g., benzene as the nonalkylated aromatic include diethylbenzene, diisopropylbenzene, dibutylbenzene, triethylbenzene, triisopropylbenzene, and so forth.

The catalyst of our invention is a surface-modified zeolite beta which results from acid washing of an as-synthesized and templated zeolite beta. That is, the formation of the surface-modified zeolite beta starts with an as-synthesized and templated beta where the template is, for example, a tetraalkylammonium salt, such as a tetraethylammonium salt. It is critical to acid wash a templated zeolite beta in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, hydrochloric acid and so forth. The acid may be used alone or may optionally contain a buffer such as ammonium nitrate, ammonium sulfate, ammonium phosphate, ammonium chloride, etc., and mixtures thereof. It is preferred to use a buffer in conjunction with the acid so that the pH does not change appreciably when the zeolite is added, thus requiring further addition of acid. For example, a 0.01 molar nitric acid may be used in conjunction with ammonium nitrate to perform the acid wash, although substantially higher concentrations, up to about 20 weight percent nitric acid, are preferred. Nitric acid is a preferred acid since it is a non-complexing acid and therefore does not encourage dealumination. Treatment of the templated zeolite beta with strong acid may be effected over the temperature range between about 20° C. up to about 125° C. It is important that acid washing be done under conditions not so -severe as to effect dealumination.

The time over which acid washing is conducted is quite temperature dependent. As mentioned previously, it is critical in the formation of the surface-modified zeolite beta of our invention that there be no significant bulk dealumination of the zeolite. Whether dealumination has occurred can be determined by the Si/Al mole ratio. For the purpose of this invention, no significant dealumination has occurred when the Si/Al mole ratio of the non-templated, calcined, surface-modified zeolite beta is within ±2 units of the Si/Al mole ratio of the as synthesized zeolite beta. Thus, as a general statement it can be said that acid washing should be done for a time insufficient to effect dealumination. For example, using 0.01 molar nitric acid and ca. 40% ammonium nitrate at 70° C., contact times of 2–3 hours are found adequate to modify the environment of surface aluminum without causing significant bulk dealumination. Using ca. 15% nitric acid with ammonium nitrate to treat an ca. 25 weight percent slurry at 85° a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550–700° C. Calcination conditions are well known in the art and need not be elaborated upon here. It also needs to be mentioned that powdered zeolite itself is not usually used. Therefore, in the more usual case after the templated zeolite beta is acid washed it is mixed with a conventional binder, extruded, and the extrudate is ultimately calcined. But it is to be understood that the critical portion of our preparation is the acid wash of the templated beta according to the foregoing description. As will be seen within, acid washing a calcined (i.e., non-templated) zeolite beta does not afford the surface-modified material of our invention.

It has been found that after treatment as described above the surface aluminum atoms are chemically modified. It is believed that the modification is in the form of replacement of strong acid sites at the catalyst surface by weaker acids sites. However, it is to be clearly understood that this is only a working hypothesis and that the success of our invention does not rest thereon. What has been definitely observed is that the surface aluminums of the modified zeolite beta of our invention have 2p binding energies as measured by x-ray photoelectron spectroscopy of at least 74.8 electron volts.

Alkylation of alkylatable compounds by the olefins of our invention may be exemplified by the alkylation of benzene with propylene. Such alkylation may be carried out in any of the ways which are well known to those practicing the art. For example, the process in general can be carried out in a batch mode by heating the catalyst, aromatic hydrocarbon, and olefin in a stirred autoclave at a temperature between 60 and 400° C. and at sufficient pressure to maintain at least a partial liquid phase. The pressure typically will be in the range of 200 to about 1000 psig, but serves only to ensure at least partial liquid phase reaction.

However, the process is more advantageously performed in the continuous mode employing a fixed bed reactor operating in an upflow or downflow mode or using a moving bed reactor operating with cocurrent or countercurrent catalyst and hydrocarbon flows. The reactors also may contain one or more catalyst beds and may be equipped for the interstage addition of olefin as well as interstage cooling. Interstage olefin addition ensures a more nearly isothermal operation and tends to enhance product quality and catalyst life. A moving bed reactor provides the advantage of continuous spent catalyst removal for regeneration and replacement by fresh or regenerated catalyst. However, it also is possible to carry out our invention using swing bed reactors.

Exemplifying the process of our invention by the alkylation of benzene with propylene, the continuous alkylation may be performed using a fixed bed reactor. Benzene and propylene may be introduced into the reactor at temperatures between 90 and 160° C. The overall benzene-to-propylene ratio may be between 2 and about 10, although normally it is between about 2.5 and about 8. Feedstock may be passed either flow or downflow, although a downflow mode is more conventional. Pressures of 200–500 psig are generally employed with flow rates being in the region of 1 to about 10 LHSV of benzene.

The following examples are only illustrative of our invention and do not limit it in any way.

EXAMPLE 1

Preparation of acid washed zeolite betas. Commercial zeolite beta, $SiO_2$ 92.2 wt. %, $Al_2O_3$ 7.0 wt. %, LOI 24.3 wt.

%, and $N_2$ BET 672 m2/g, identified as sample A in the following examples, was calcined in air at 650° C. for 2 hours. To a solution of 1428 grams ammonium nitrate in 3224 grams distilled water was added 932 grams of 70 weight percent nitric acid and the mixture was heated to 85°C. The calcined zeolite beta (1416 grams dry weight) was added and this mixture was stirred at 85° C. for 90 minutes. The slurry was filtered and washed using 10 liters of distilled water and then dried at 100° C. for 16 hours. Analysis showed a molar $SiO_2/Al_2O_3$ ratio of 137, $SiO_2$ 96.8 wt. %, $Al_2O_3$ 1.2 wt %, $N_2$ BET surface area 720 m2/g. This sample is identified as sample B in the following examples.

Sample C was prepared essentially as described for sample B except that 10% less nitric acid was used (839 grams 70% nitric acid). Analyses showed $SiO_2$ 93.6 wt. %, $Al_2O_3$ 1.5 wt. %, molar ratio $SiO_2/Al_2O_3$ 105, surface area 689 m2/g.

Samples D and E were prepared essentially as described for sample B except that uncalcined zeolite beta powder was used as the raw material. The acid-treated material prior to calcination corresponds to sample D; material calcined after acid treatment (650° C. for 3 hours in air) corresponds to sample E. Analyses on E showed 91.7 wt. % $SiO_2$, 6.1 wt. % $Al_2O_3$, molar ratio $SiO_2/Al_2O_3$ 25.5.

The samples were examined by x-ray photoelectron spectroscopy (XPS) to determine binding energies as well as the surface silicon:aluminum atomic ratios. The results are summarized in Table 1.

TABLE 1

| Peak | A | B | C | D | E |
|---|---|---|---|---|---|
| Binding Energies (eV) | | | | | |
| Al2p | 74.65 | 74.18 | 74.13 | 74.07 | 75.20 |
| Si2p | 103.30 | 103.30 | 103.30 | 103.30 | 103.30 |
| C 1s | 284.48 | | | 285.18 | |
| C 1s | 286.80 | | | 286.44 | |
| C 1s | 288.80 | | | | |
| O 1s | | | | 530.52 | |
| O 1s | 532.53 | 532.44 | 532.45 | 532.47 | 532.43 |
| Surface Concentrations (atomic %) | | | | | |
| Al | 1.83 | 0.41 | 0.35 | 1.44 | 1.93 |
| Si | 26.66 | 30.99 | 31.88 | 24.28 | 29.91 |
| Si/Al (bulk) | ≈15 | ≈68 | ≈53 | ≈15 | ≈13 |
| Si/Al(XPS) | 15 | 76 | 91 | 17 | 16 |

The binding energies of Si2p and O1s are typical for highly siliceous zeolites. It is noteworthy that the Al2p binding energy for the reference sample A is about 0.5 eV higher than for all acid washed samples. This indicates that the aluminum in the precursor sample is most likely in the framework. The Al2p binding energy of about 74.1 eV for all acid washed samples is more typical of free alumina. It also is noteworthy that for the acid washed and calcined sample E the Al2p binding energy is about 0.5 eV higher than for the reference sample. It also is seen that the surface and bulk Si/Al ratios are about the same within the uncertainties associated with measurements of very low Al concentrations.

These data strongly indicate that the surface aluminum concentration has not been reduced relative to the bulk aluminum concentration (i.e., there has been no surface dealumination) and also indicates that the nature of aluminum on the surface has been altered.

EXAMPLE 2

Alkylation of benzene with propylene using various zeolite betas. In all cases the samples described above which were used in reactor testing were bound with alumina (70/30 zeolite /binder), extruded (1/16" extrudates), dried, then calcined at 650° C. for 2 hours. For each test 10 cc of 1/16" extrudates were loaded into a reactor to form a bed ½" in diameter and 3 ¾" to 4" long. The catalyst was activated for 12 hours by passing a stream of benzene over the catalyst at 140° C., 500 psig and 6 benzene LHSV. Temperature was adjusted to the desired run temperature and the feed switched to a blend of 6 weight percent propylene in benzene at 6 LHSV. The position of the maximum temperature (due to the exothermic reaction) in the bed was noted. Deactivation was determined by noting the position of the maximum temperature after 48 hours at test conditions. Deactivation is calculated by taking the difference in these two positions (in inches), dividing by the bed length (in inches) and then dividing by the time interval (in days). The results are multiplied by 100% to give a deactivation rate in percent of catalyst bed/day.

Two catalyst samples (I, II) prepared by first calcining the zeolite beta as a powder followed by acid washing, were tested at 130° C. Sample I and II are analogous to samples B and C of the prior example. Both catalysts exhibited propylene breakthrough before the end of the 48 hour test period, resulting in 100% deactivation or ≦50%/day. The catalyst of the invention, III, analogous to sample E of the prior example, was tested at 130° with the results shown in the table.

| Catalyst | Deactivation (%/day) |
|---|---|
| I | >50 |
| II | >50 |
| III | 10.3 |

These results, obtained under experimental conditions as identical as possible save for the catalyst, unequivocally demonstrate the vast superiority of our catalysts.

What is claimed is:

1. A process for preparing a non-templated surface-modified calcined zeolite beta comprising treating an as synthesized and templated zeolite beta with an acid at a pH between about 0 and about 2 at a temperature from about 20° C. up to about 125° C. for a time sufficient to chemically modify the surface aluminum atoms such that the surface aluminum atoms have 2p binding energies, as measured by x-ray photoelectron spectroscopy, of at least 74.8 electron volts and such that the Si/Al mole ratio of the acid treated zeolite beta is within ±2 units of the Si/Al mole ratio of the as synthesized zeolite beta and then calcining the acid treated templated zeolite beta at a temperature from about 550° to about 700° C. for a time sufficient to remove the template.

2. The process of claim 1 where the acid also contains a buffer.

3. The process of claim 2 where the buffer is selected from the group consisting of ammonium nitrate, ammonium phosphate, ammonium sulfate, ammonium chloride and mixtures thereof.

4. The process of claim 1 where the acid is selected from the group consisting of nitric acid, phosphoric acid, sulfuric acid and hydrochloric acid.

* * * * *